(12) United States Patent
Ceccato et al.

(10) Patent No.: US 10,449,289 B2
(45) Date of Patent: Oct. 22, 2019

(54) ELEVATOR DEVICE FOR INTRAVENOUS SOLUTION

(71) Applicant: A.L.M.S. Medical S.r.l., Velletri (IT)

(72) Inventors: Serena Ceccato, Fiesso d'Artico (IT); Giorgia Zuccolin, Venezia Chirignago (IT)

( * ) Notice: Subject to any disclaimer, the term of this patent is extended or adjusted under 35 U.S.C. 154(b) by 0 days.

(21) Appl. No.: 16/081,910

(22) PCT Filed: Feb. 28, 2017

(86) PCT No.: PCT/IB2017/051155
§ 371 (c)(1),
(2) Date: Sep. 2, 2018

(87) PCT Pub. No.: WO2017/149444
PCT Pub. Date: Sep. 8, 2017

(65) Prior Publication Data
US 2019/0076598 A1    Mar. 14, 2019

(30) Foreign Application Priority Data

Mar. 1, 2016  (IT) .......................... UB2016U3113 U

(51) Int. Cl.
*A61M 5/14*  (2006.01)
*A45C 9/00*  (2006.01)
(Continued)

(52) U.S. Cl.
CPC ............. *A61M 5/1415* (2013.01); *A45C 9/00* (2013.01); *A45C 11/00* (2013.01); *A45C 13/02* (2013.01); *A45C 2200/15* (2013.01)

(58) Field of Classification Search
CPC ........ A61M 5/1415; A45C 9/00; A45C 11/00; A45C 13/02; A45C 2200/15
See application file for complete search history.

(56) References Cited

U.S. PATENT DOCUMENTS 2,245,999 A * 6/1941 Plotkin .................. A45C 13/02
190/109
2,835,520 A * 5/1958 Schiring .............. A61B 6/4464
248/333

(Continued)

FOREIGN PATENT DOCUMENTS

| CA | 2871810 | 5/2016 |
| DE | 3825666 | 9/1989 |
| WO | 2016160676 | 10/2016 |

*Primary Examiner* — Anita M King
(74) *Attorney, Agent, or Firm* — Themis Law

(57) ABSTRACT

An elevator device for intravenous solution includes an openable container with a base and a lid, a pole having at least two segments and adapted to define a more extended condition and a less extended condition, and a member supporting a bag or a bottle containing the intravenous solution. The elevator device is adapted to assume a first non-operating configuration, in which the pole in the less extended condition and the member are accommodated into a seat provided in the container, and a second operating configuration, in which the pole is in the more extended condition and the member is associated to the pole at an upper portion thereof, and in which the container defines a supporting base that inferiorly supports the pole and that is adapted to be stably positioned on a resting surface.

19 Claims, 3 Drawing Sheets

(51) Int. Cl.
*A45C 11/00* (2006.01)
*A45C 13/02* (2006.01)

(56) References Cited

U.S. PATENT DOCUMENTS

| | | | | |
|---|---|---|---|---|
| 3,311,202 A | * | 3/1967 | Schell | A45C 3/02 |
| | | | | 190/16 |
| 4,471,933 A | | 9/1984 | Nelson | |
| 4,744,536 A | * | 5/1988 | Bancalari | A61M 5/1415 |
| | | | | 248/125.8 |
| 6,036,147 A | * | 3/2000 | Militzer | A61M 5/1415 |
| | | | | 248/125.8 |
| 7,285,111 B2 | * | 10/2007 | Gaster | A61M 5/1415 |
| | | | | 604/131 |
| 7,559,516 B2 | * | 7/2009 | Koder | A47B 9/04 |
| | | | | 108/147 |
| 8,567,730 B1 | * | 10/2013 | Stevenson | A61M 5/1415 |
| | | | | 248/125.8 |
| 9,370,617 B2 | * | 6/2016 | Chepurny | A61G 12/008 |
| 9,375,064 B1 | | 6/2016 | Nuculaj | |
| 9,554,631 B1 | * | 1/2017 | Bongiorno | A45C 5/03 |
| 2005/0040126 A1 | * | 2/2005 | Gaster | A61M 5/1415 |
| | | | | 211/207 |
| 2009/0314923 A1 | * | 12/2009 | Timoszyk | A61M 5/1415 |
| | | | | 248/647 |
| 2013/0153351 A1 | | 6/2013 | House, III | |
| 2016/0317392 A1 | * | 11/2016 | Harris | A61J 15/0026 |

* cited by examiner

ELEVATOR DEVICE FOR INTRAVENOUS SOLUTION

FIELD OF THE INVENTION

The present invention relates to an improved elevator device for intravenous solutions.

BACKGROUND OF THE INVENTION

Elevator devices for intravenous solution are known, better known as "i.v. stands", which consist of a pole inferiorly associated with a base, generally provided with rollers, and also provided with one or more support arms for bags or bottles of fluid intended to be infused into the patient. In particular, the support arm with the corresponding fluid bag is positioned, even in an adjustable manner, at a suitable height along the pole in order to generate the prevalence needed for the fluid in the bag to be infused into the patient.

However, these devices have a fixed configuration which is rather cumbersome, especially when their use is not required.

Moreover, they are substantially adapted to be used only in hospitals or health resorts or anyway in places characterized by regular resting surfaces for the base of the pole. In particular, to date, no devices are known which can be used in emergency rooms, where instead an operator generally manually supports the fluid bag in a raised position.

In essence, traditional devices for supporting bags or bottles containing intravenous solutions at the desired height are not completely satisfactory in that they do not adequately combine technological aspects and functional requirements.

SUMMARY OF THE INVENTION

It is the object of the invention to provide an improved elevator device for intravenous solution which is usable in any context, and in particular is not cumbersome when it does not need to be used.

It is another object of the invention to provide a device which is easily carried.

It is another object of the invention to provide a device which is particularly effective and versatile.

It is another object of the invention to implement a device which has suitable sanitization, usability, systemic and environmental compatibility features.

It is another object of the invention to implement a device which has the necessary properties for the functionality thereof to be the highest in the context of emergency procedures.

It is another object of the invention to implement a device which is also installable and usable outdoors and/or in any case outside of the healthcare and/or hospital environment.

It is another object of the invention to implement a device which, in addition to the function of supporting the intravenous solution in a raised position, has additional features.

It is another object of the invention to implement a device which can be obtained in a simple, quick and cost-effective manner.

It is another object of the invention to implement a device which has an alternative and/or improving characterization, both from a structural and functional point of view compared to those already known.

All these objects, both alone or in any combination thereof, and others which will become apparent from the following description are achieved, according to the invention, with a device having the features described hereinafter.

BRIEF DESCRIPTION OF THE DRAWINGS

The present invention is further clarified hereinafter in a preferred embodiment thereof, with reference to the accompanying drawings, in which.

DETAILED DESCRIPTION OF EMBODIMENTS OF THE INVENTION

Figure 1:
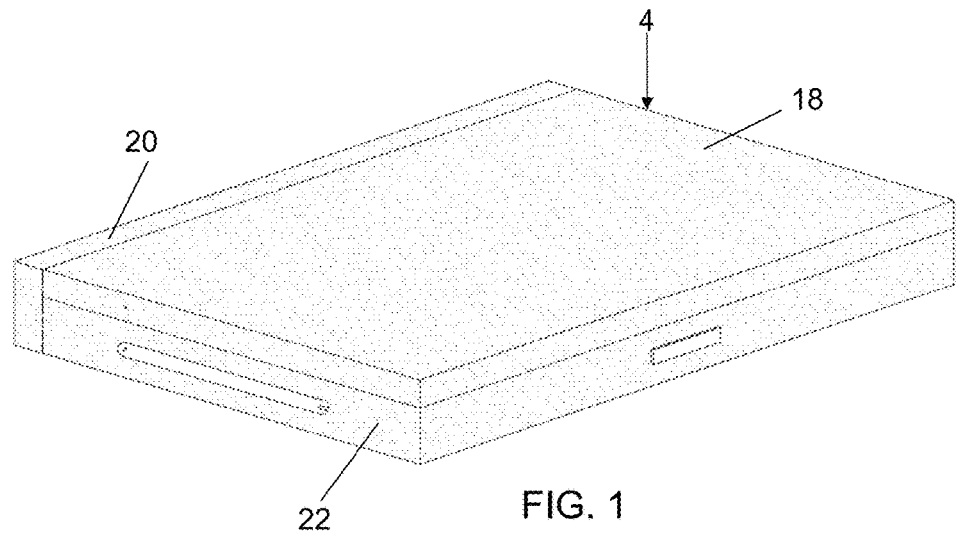
FIG. 1 shows a perspective view of an improved device according to the invention in a closed, non-operating configuration.

As can be seen from the figures, the improved device 2 according to the invention comprises a container 4, shaped as a suitcase, preferably parallelepiped in shape, with at least one handle, in which a housing seat 6 is provided for a pole 10, which comprises at least two segments 8 configured to define at least one more extended condition and one less extended condition, of short longitudinal length, of the pole itself.

Pole 10 is preferably assembled so that its more extended condition is that in which it is assembled, and so that its less extended condition is that in which the pole itself is disassembled.

Preferably, pole 10 is telescopic, although it is contemplated that it can consist of independent segments 8 sequentially constrained to one another. Advantageously, the telescopic pole 10 can be motorized so as to allow the automatic extension and/or the shortening of the segments 8 thereof.

Conveniently, container 4 has dimensions suitable for transport by hand and for accommodating a backpack therein. For example, typical dimensions may be about 30 cm×40 cm×4 cm.

Advantageously, container 4 is made of a material which is simultaneously light and ensures a high protection of the content thereof. For example, container 4 can be made of aluminum, plastic or the like.

A member 12 is also provided, intended to support a bag 13 or a bottle containing the intravenous solution. Conveniently, such a member comprises one or more hooks to which one or more bags or bottles of intravenous solution can be hung.

Such a member 12 may be made separately from pole 10 and provided with means for easily, safely and removably constraining it to the pole itself. In this case, advantageously, a housing seat 11 may be provided within container 4 for such a member 12.

Alternatively, member 12 may always remain associated with pole 10, even when the latter is accommodated in the housing seat 6 thereof; in particular, in that case, member 12 is articulated to pole 10 so as to switch between an operating condition, in which it substantially projects or is perpendicular with respect to the pole, and a non-operating condition, of smaller dimensions, in which it is substantially aligned and parallel to the pole itself.

Preferably, among segments 8, that intended to define the lower element of pole 10 in the assembled condition has the lower end shaped as a tip 14.

The device 2 according to the invention is also provided with means associated with and/or included in the container 4 so that the latter defines a stable supporting base which inferiorly supports said pole, in extended and assembled condition, and which is intended to be stably positioned on a support surface, which may be the ground, the floor and/or any resting base of a cabinet, for example, or the like.

In particular, these means comprise a folding lid 18, which is associated with a preferably flat base 22 of container 4, and which conveniently has dimensions suitable for protecting the content of the container itself.

More in detail, the lid 18 of container 4 is articulated to a longitudinal side 20 thereof, which in turn is articulated to the base 22 of the same container 4 and is provided with a through hole 24 intended to be crossed by pole 10 in extended and assembled condition.

However, the invention contemplates that in order to define the support base of the assembled pole 10, different support bases may be used in place of lid 18 and/or base 22, such as tripods, foldable poles and the like, which can be advantageously accommodated inside container 4.

Conveniently, pole 10 in the less extended condition, preferably disassembled, occupies a small space within container 4 and, advantageously, more housing seats may be provided within the latter for catheters 23 to be associated with the bag of the intravenous solution 13, as well as for other tools useful in emergency operations, and in particular a lamp 25, an electric battery 26 with a corresponding electrical socket 27, a refrigerating room 28 for drugs, haemostatic laces 29, a three-way cock fitting 30, patches 31, an infusion tube 32, a cannula needle set 33, a camera, a radio transmitter, etc.

The operation of the improved elevator device 2 according to the invention clearly appears from the foregoing description.

In particular, device 2 can take a first non-operating disassembled configuration, particularly suitable for transport. In this configuration, container 4 is closed and pole 10, which is in its less extended condition (i.e. of smaller longitudinal dimension), is accommodated inside the corresponding seat 6 provided in container 4. In particular, lid 18 covers base 22 so as to define an inner housing space therebetween which is separated from the surrounding environment.

In the case of removable member 12, the latter is disassembled from pole 10 and is conveniently accommodated inside the respective seat 11 provided in container 4; instead, in the version with the member 12 remaining always articulated to pole 10 at an upper area thereof, such a member is folded so as to be substantially parallel to pole 10, in a non-operating condition of smaller dimensions, and is accommodated with the pole itself within seat 6.

When there is an operating need, the user switches device 2 from the disassembled, non-operating configuration to the assembled operating configuration. In particular, to this end, he/she lifts the lid 18 of container 4 and, after having extracted segments 8 from base 22, he/she assembles them together in order to assemble pole 10 and thus bring it to a more extended condition. Conveniently, in the case of telescopic pole 10, the user slides segments 8 or, in the case of motorized pole, operates the automatic extension thereof.

Moreover, in the case of removable member 12, the user pulls the support member 12 of the infusion bag and stably constrains it to pole 10 at the top area thereof. Instead, in the case of the member 12 articulated to pole 10, the user rotates such a member about its pivot pin with the pole so as to bring it to its operating condition, in which it projects laterally, and is preferably perpendicular, with respect to the pole itself.

Thereafter (or possibly even before the assembly of pole 10), the user flips container 4 and turns it into a stable supporting base for pole 10 assembled in more extended condition.

Figure 2:
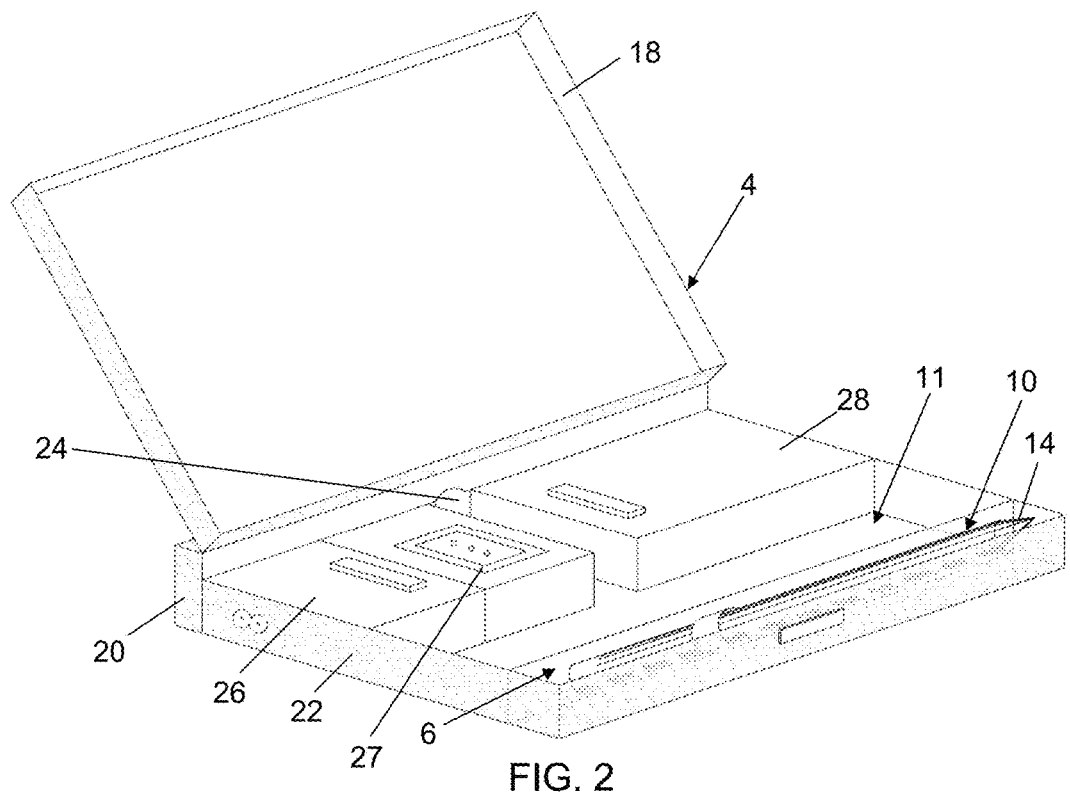
FIG. 2 shows it in an open, non-operating configuration.
Figure 3:
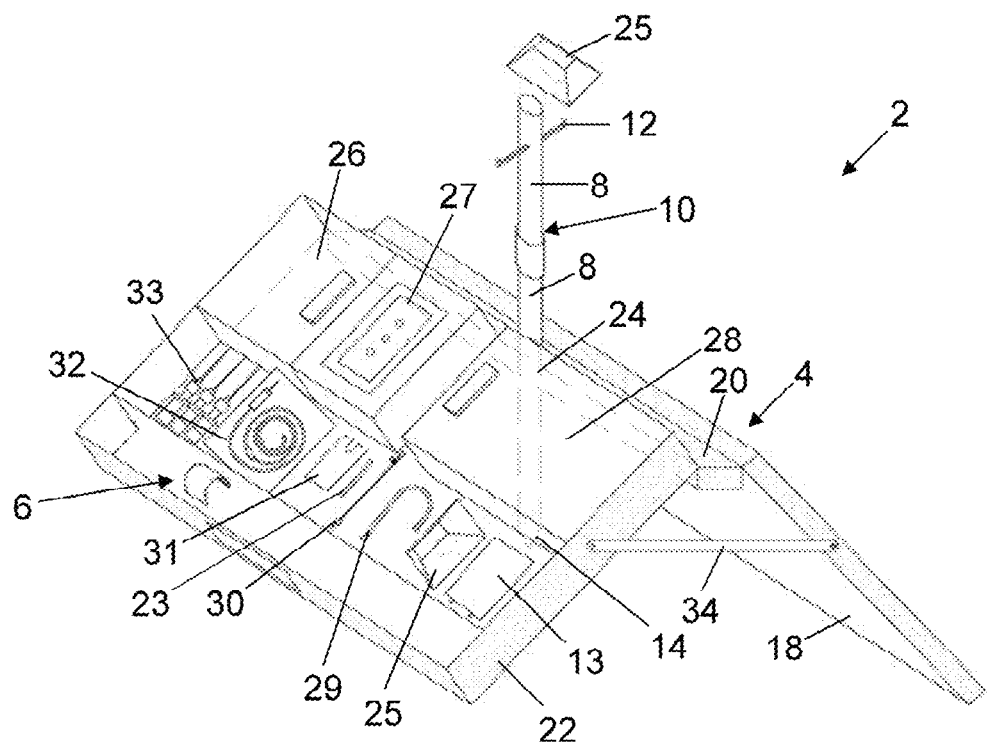
FIG. 3 shows a perspective view thereof in an operating configuration.

In particular, in the first embodiment shown in FIGS. 1 to 3, container 4 rests on a support surface with a longitudinal edge of base 22 and with the corresponding longitudinal edge of lid 18, as shown in FIG. 3.

Conveniently, the base 22 of container 4 and the lid 18 are maintained in the spread apart position by a pair of mutual connection and stabilization tie rods 34.

Then, once the stable supporting base has been created, the lower segment 8 of the assembled pole 10 is passed through hole 24 until the tip 14 of such a segment rests on or penetrates into the resting surface of the device.

Conveniently, the supporting base for the assembled pole 10 is thus stable while allowing free and easy access to the lower section of the pole itself.

Figure 4:
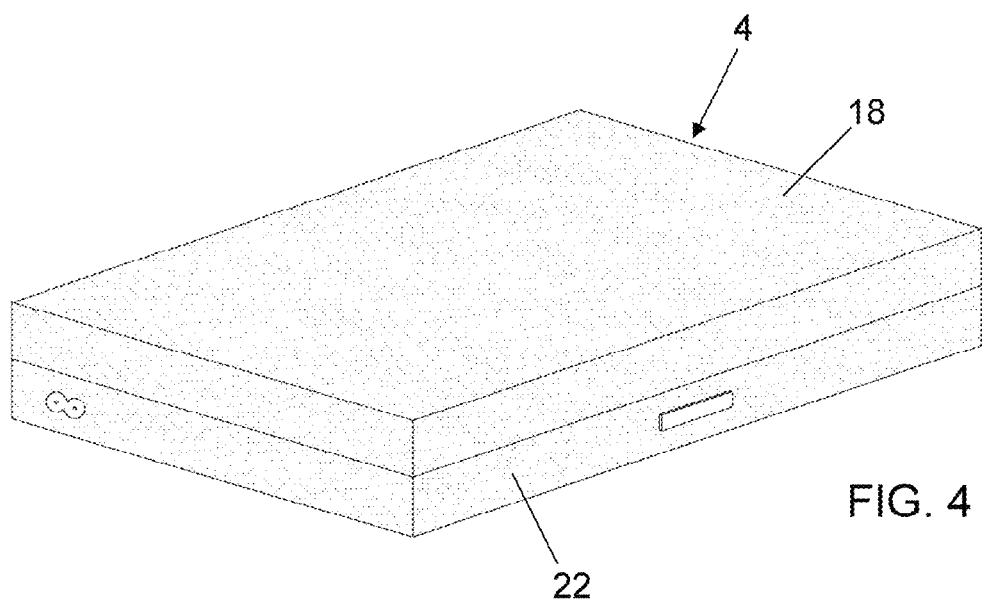
FIG. 4 shows a perspective view of a different embodiment of the device according to the invention in the same condition as in FIG. 1.
Figure 5:
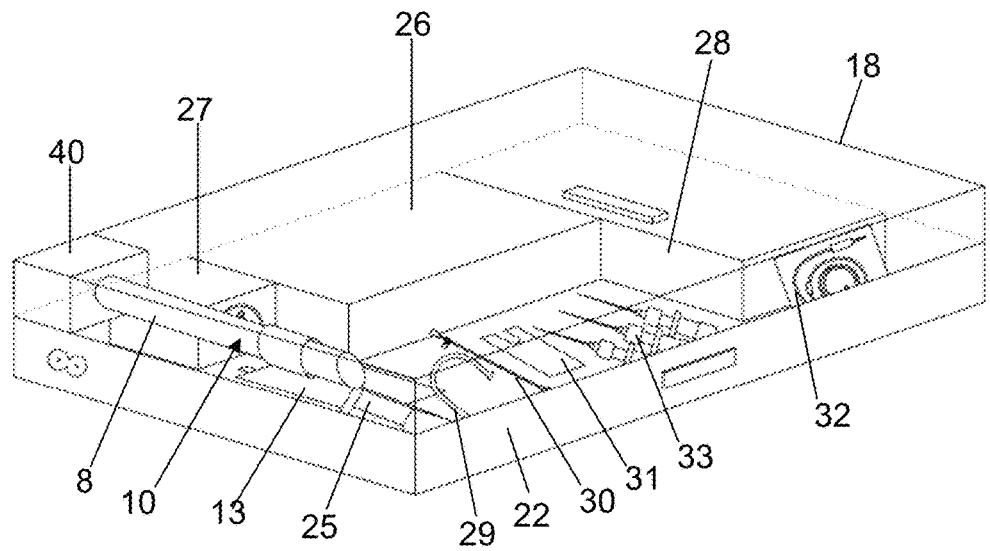
FIG. 5 shows it as in FIG. 4 but with the lid in phantom.
Figure 6:
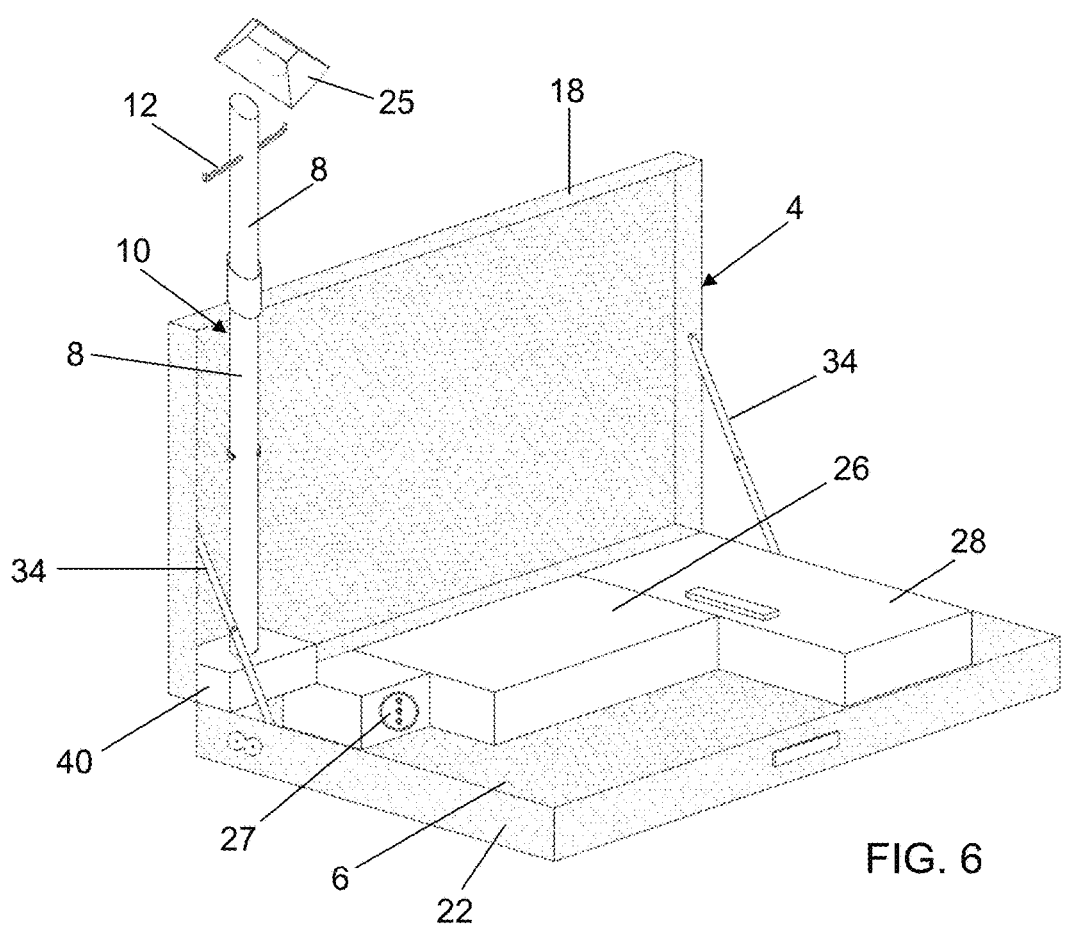
FIG. 6 shows the device in FIG. 4 in an open operating configuration.

In a second embodiment shown in FIGS. 4 to 6, the device has all the features described above with reference to the first embodiment, and has the same operating mode, except for the lower end of pole 10 always remaining associated with the inner walls of the lid 18 and/or of the base 22 of container 4, as well as for the fact that no through hole 24 is provided in the latter, intended to be crossed by pole 10 in a more extended/assembled condition.

In particular, in the embodiment shown in FIGS. 4 to 6, the lower end of pole 10 is constrained to a connecting block 40 which is in turn constrained to the inner wall of the folding lid 18 of container 4.

Advantageously, lid 18 is directly articulated to the base 22 of container 4 itself, but could be articulated to the latter through a side 20 thereof.

Also in this second embodiment, device 2 can take a first non-operating disassembled configuration, particularly suitable for transport. In this configuration, the folding lid 18 closes and superiorly covers base 22, and pole 10 is in the less extended/disassembled condition and is constrained, by means of the connecting block 40 thereof, to the lid 18 so as to be accommodated into the corresponding seat 6 provided into the base 22 of container 4.

When there is an operating need, the user switches device 2 from the disassembled, non-operating configuration to the assembled operating configuration. In particular, to this end, he/she lifts the lid 18 of container 4, preferably by tilting it by 90° with respect to base 22, so as to also cause the rotation of the corresponding block 40, associated with lid 18, and thus arrange the lower segment 8 of pole 10 in a substantially vertical position. Once this position has been reached, the remaining segments 8 are assembled together to bring pole 10 to a more extended condition or, in the case of telescopic pole, are manually or automatically slid so as to cause the extension of the pole itself.

Conveniently, in this configuration, lid 18 also acts as a lateral support for pole 10.

In this second embodiment, the outer surface of base 22 defines the supporting base intended to be stably positioned on a resting surface.

Conveniently, also in this second embodiment, the base 22 of container 4 and the lid 18 are maintained in the spread apart position shown in FIG. 6 by a pair of stabilizing hooks 34.

From the foregoing description, it is apparent that the device according to the invention is particularly advantageous, since:

in the non-operating disassembled configuration, it is compact and easily transportable, in the assembled operating configuration, it is very stable and adapted to be used on any type of resting surface, even outdoors and on uneven ground, it consists of particularly simple components and therefore is very cost-effective to be manufactured, it allows to switch from the non-operating to the operating use configuration in a particularly simple and quick manner.

The invention claimed is:

1. An improved elevator device (2) for intravenous solution, comprising:
   an openable container, which is shaped as a suitcase and has a base (22) and a lid (18) comprising an at least partially flat surface;
   a pole (10), which comprises at least two segments (8) comprising an upper segment and a lower segment and is configured to assume at least one more extended condition and one less extended condition of said pole (10); and
   a member (12) adapted to support a bag (13) or a bottle containing the intravenous solution, said member (12) comprising at least one hook to which said bag (13) or said bottle of the intravenous solution is intended to be hung, wherein the elevator device is configured to have:
   a first non-operating configuration, in which said pole (10), which is in said less extended condition, and the member (12) are accommodated into at least one seat (6, 11), provided in the container (4), in said first non-operating configuration, and in which said container (4) is in a closed condition with said lid (18) covering said base (22), and
   a second operating configuration, in which said pole (10) is in the more extended condition, in which said member (12) is engaged with said pole at an upper portion thereof, and in which said container (4) defines a supporting base that inferiorly supports said pole (10) and that is intended to be stably positioned on a resting surface, in said second operating configuration, the supporting base for the pole (10) being defined by at least one of said lid (18) or by said base (22) of the container (4),
   wherein a lower end of the lower segment (8) of said pole (10) is shaped as a tip (14) to penetrate, at least in part, into said resting surface.

2. The device according to claim 1, wherein, in said second operating configuration, said container (4) defines the supporting base for supporting said pole (10), which is configured to rest with a lower end thereof on said resting surface.

3. The device (10) according to claim 1, wherein said pole (10) is assemblable, and wherein:
   said more extended condition corresponds to a condition in which said pole (10) is assembled, and
   said less extended condition corresponds to a condition in which said pole (10) is disassembled, and
   wherein said pole (10) is assemblable and the at least two segments comprise at least two independent segments (8), which are sequentially constrainable to each other.

4. The device (10) according to claim 1, wherein said pole (10) is telescopic.

5. The device (10) according to claim 1, wherein said pole (10) is motorized to allow an automatic extension and retraction of the at least two segments (8) thereof.

6. The device according to claim 1, wherein said container (4) is made of a lightweight material having such strength as to ensure a protection of a content of said container.

7. The device according to claim 1, wherein, in said second operating configuration, said lid (18) and said base (22) of the container (4) are arranged mutually apart, and wherein an entire outer flat surface of the base (22) of the container (4) stably rests on said resting surface.

8. The device (10) according to claim 1, wherein, in said second operating configuration, said supporting base is defined by an essentially flat outer surface of the base (22) of the container (4).

9. The device according to claim 1, wherein, in said second operating configuration, the lid (18) is rotated by about 90° with respect to the base (22) of said container (4) so that said lid (18) or said base (22) laterally supports the lower segment (8) of the pole (10), which is in a substantially vertical position.

10. The device according to claim 1, wherein said container (4) further comprises at least one housing seat for at least one tool usable in emergency situations and selected from the group consisting of: a lamp (25), an electric battery (26) with a corresponding electrical socket (27), a refrigerating room (28) for drugs, haemostatic laces (29), a three-way cock fitting (30), patches (31), and infusion tube (32), a cannula needle set (33), a camera, or a radio transmitter.

11. The device according to claim 1, wherein said member (12) is made separately from the pole (10) and is provided with a second member removably constraining said member to the pole.

12. The device according to claim 11, wherein, in said first non-operating configuration of the device, said member (12) is accommodated into a second corresponding seat (11) provided in the container (4), and wherein, in said second operating configuration of the device, said member (12) is stably associated, by said second member, with the pole (10) at the upper portion thereof.

13. The device according to claim 1, wherein said member (12) is articulated to the pole (10) and remains associated therewith both in said first non-operating and in said second operating configuration.

14. The device (10) according claim 1, wherein said member (12) is engaged with the pole (10) at a pivot pin, and wherein:
   during said first non-operating configuration, said member (12) is rotated about said pivot pin so as to be arranged substantially aligned with the pole (10), which is in the less extended condition, and
   during said second operating configuration, said member (12) is rotated about said pivot pin so as to project laterally with respect to the pole (10), which is in the more extended condition.

15. An improved elevator device (2) for intravenous solution, comprising:
   an openable container, which is shaped as a suitcase and has a base (22) and a lid (18) comprising an at least partially flat surface;
   a pole (10), which comprises at least two segments (8) comprising an upper segment and a lower segment and is configured to assume at least one more extended condition and one less extended condition of said pole (10); and
   a member (12) adapted to support a bag (13) or a bottle containing the intravenous solution, said member (12)

comprising at least one hook to which said bag (13) or said bottle of the intravenous solution is intended to be hung, wherein the elevator device is configured to have:
- a first non-operating configuration, in which said pole (10), which is in said less extended condition, and the member (12) are accommodated into at least one seat (6, 11), provided in the container (4), in said first non-operating configuration, and in which said container (4) is in a closed condition with said lid (18) covering said base (22), and
- a second operating configuration, in which said pole (10) is in the more extended condition, in which said member (12) is engaged with said pole at an upper portion thereof, and in which said container (4) defines a supporting base that inferiorly supports said pole (10) and that is intended to be stably positioned on a resting surface, in said second operating configuration, the supporting base for the pole (10) being defined by at least one of said lid (18) or by said base (22) of the container (4),
- wherein said lid (18) and said base (22) of the container (4) are mutually articulated, and wherein in said second operating configuration, said lid and said base are arranged mutually apart and each rest with a side, opposite to a side of mutual articulation, on said resting surface.

16. An improved elevator device (2) for intravenous solution, comprising:
- an openable container, which is shaped as a suitcase and has a base (22) and a lid (18) comprising an at least partially flat surface;
- a pole (10), which comprises at least two segments (8) comprising an upper segment and a lower segment and is configured to assume at least one more extended condition and one less extended condition of said pole (10); and
- a member (12) adapted to support a bag (13) or a bottle containing the intravenous solution, said member (12) comprising at least one hook to which said bag (13) or said bottle of the intravenous solution is intended to be hung, wherein the elevator device is configured to have:
- a first non-operating configuration, in which said pole (10), which is in said less extended condition, and the member (12) are accommodated into at least one seat (6, 11), provided in the container (4), in said first non-operating configuration, and in which said container (4) is in a closed condition with said lid (18) covering said base (22), and
- a second operating configuration, in which said pole (10) is in the more extended condition, in which said member (12) is engaged with said pole at an upper portion thereof, and in which said container (4) defines a supporting base that inferiorly supports said pole (10) and that is intended to be stably positioned on a resting surface, in said second operating configuration, the supporting base for the pole (10) being defined by at least one of said lid (18) or by said base (22) of the container (4),
- wherein said lid (18) is articulated to a side (20) of the container (4), and wherein said side (20) is in turn articulated to said base (22) and is provided with a through hole (4), which is dimensioned to be crossed by said pole (10) when said device is in said second operating configuration.

17. The device (10) according to claim 16, wherein in said second operating configuration, said supporting base is defined by:
- said base (22) of said container (4), which rests with a second side thereof on said resting surface, and by
- said lid (18), which is tilted so that a non-articulated side thereof rests on said resting surface,
- and wherein said base (22) of said container (4) and said lid (18) face each other and are adapted to be inclined in opposite directions so that said side (20) of the container (4) is substantially horizontal and parallel to said resting surface.

18. An improved elevator device (2) for intravenous solution, comprising:
- an openable container, which is shaped as a suitcase and has a base (22) and a lid (18) comprising an at least partially flat surface;
- a pole (10), which comprises at least two segments (8) comprising an upper segment and a lower segment and is configured to assume at least one more extended condition and one less extended condition of said pole (10); and
- a member (12) adapted to support a bag (13) or a bottle containing the intravenous solution, said member (12) comprising at least one hook to which said bag (13) or said bottle of the intravenous solution is intended to be hung, wherein the elevator device is configured to have:
- a first non-operating configuration, in which said pole (10), which is in said less extended condition, and the member (12) are accommodated into at least one seat (6, 11), provided in the container (4), in said first non-operating configuration, and in which said container (4) is in a closed condition with said lid (18) covering said base (22), and
- a second operating configuration, in which said pole (10) is in the more extended condition, in which said member (12) is engaged with said pole at an upper portion thereof, and in which said container (4) defines a supporting base that inferiorly supports said pole (10) and that is intended to be stably positioned on a resting surface, in said second operating configuration, the supporting base for the pole (10) being defined by at least one of said lid (18) or by said base (22) of the container (4),
- wherein the lower segment (8) of said pole (10) is constrained to one or both of inner walls of said lid (18) or of said base (22) of the container (4).

19. An improved elevator device (2) for intravenous solution, comprising:
- an openable container, which is shaped as a suitcase and has a base (22) and a lid (18) comprising an at least partially flat surface;
- a pole (10), which comprises at least two segments (8) comprising an upper segment and a lower segment and is configured to assume at least one more extended condition and one less extended condition of said pole (10); and
- a member (12) adapted to support a bag (13) or a bottle containing the intravenous solution, said member (12) comprising at least one hook to which said bag (13) or said bottle of the intravenous solution is intended to be hung, wherein the elevator device is configured to have:
- a first non-operating configuration, in which said pole (10), which is in said less extended condition, and the member (12) are accommodated into at least one seat (6, 11), provided in the container (4), in said first non-operating configuration, and in which said container (4) is in a closed condition with said lid (18) covering said base (22), and a second operating configuration, in which said pole (10) is in the more extended condition, in which said member (12) is engaged with said pole at an upper portion thereof, and in which said container (4) defines a supporting base that inferiorly supports said pole (10) and that is intended to be stably positioned on a resting surface, in said second operating configuration, the supporting base for the pole (10) being defined by at least one of said lid (18) or by said base (22) of the container (4), wherein said base (22) and said lid (18) of said container (4) are connected to each other by at least one stabilizer tie rod (34).

* * * * *